United States Patent [19]

Riefling et al.

[11] Patent Number: 5,262,556
[45] Date of Patent: Nov. 16, 1993

[54] PROCESS FOR THE REACTION OF HALOGENATED AROMATICS WITH ELECTROPHILES

[75] Inventors: Bernard Riefling; Jürgen Seubert, both of Darmstadt; Volker Reiffenrath, Rossdorf; Reinhard Hittich, Modautal, all of Fed. Rep. of Germany

[73] Assignee: Merck Patent Gesellschaft mit beschränkter Haftung, Darmstadt, Fed. Rep. of Germany

[21] Appl. No.: 879,238

[22] Filed: May 6, 1992

[30] Foreign Application Priority Data

Jan. 20, 1992 [DE] Fed. Rep. of Germany ....... 4201308

[51] Int. Cl.$^5$ .......................... C07F 5/02; C07F 5/04; C07F 7/08; C07C 25/00
[52] U.S. Cl. ..................... 556/445; 556/466; 556/489; 556/454; 558/287; 558/288; 558/298; 570/129; 570/141; 570/163; 570/143; 570/171; 546/345
[58] Field of Search ............... 570/127, 129, 163, 143, 570/171; 556/478, 445, 466, 489, 454; 558/288, 294, 287, 298; 546/345

[56] References Cited

U.S. PATENT DOCUMENTS 5,087,764  2/1992  Rieffenrath et al. ............... 568/656

FOREIGN PATENT DOCUMENTS 0238272  9/1987  European Pat. Off. .
0440082-A2  8/1991  European Pat. Off. .

OTHER PUBLICATIONS

Ladd, David L. et al., J. Org. Chem., 1981, vol. 46, pp. 203-206.

*Primary Examiner*—Joseph Paul Brust
*Attorney, Agent, or Firm*—Millen, White, Zelano & Branigan

[57] ABSTRACT

The invention relates to a process for the reaction of fluorinated or chlorinated aromatics with electrophiles at the ortho position relative to the fluorine or chlorine atom, characterized in that a strong base is added to a mixture of the fluorinated or chlorinated aromatic and the electrophile.

11 Claims, No Drawings

PROCESS FOR THE REACTION OF HALOGENATED AROMATICS WITH ELECTROPHILES

The invention relates to a process for the reaction of halogenated aromatics with electrophiles at the ortho position relative to the halogen atom, in which a strong base is added to a mixture of the halogenated aromatic and the electrophile.

Halogenated aromatics substituted in the ortho position relative to the halogen atom are important intermediates in industrial organic chemistry. Suitably substituted derivatives are in particular valuable intermediates for the synthesis of high-value end products or are themselves such end products for the electronics industry, for example liquid crystals, for crop protection, for example pesticides, or for the preparation of pharmaceutically highly active substances, for example dopamine receptor blockers, antiemetics or antipsychotics.

The prior art processes for the preparation of these compounds are not suitable for large-scale production but are processes which can be carried out without risk only on a laboratory scale.

Thus, for example, the metallation described by D. L. Ladd in J. Org. Chem. 46, 203 (1981) of 1,4-di-fluoro-benzene with butyllithium at <-65° C. produces 2,5-difluorophenyllithium, which is reacted at the same (low) temperature with trimethyl borate to give dimethyl 2,5-difluorophenylboronate.

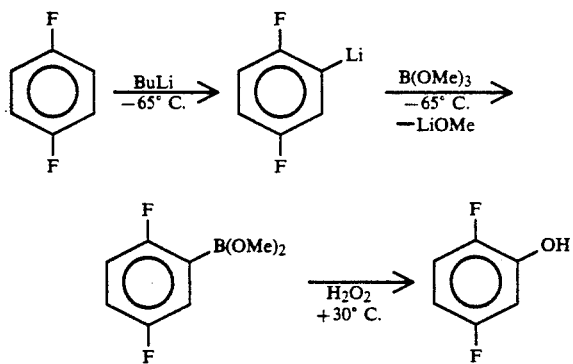

The corresponding phenol is formed from the boronate by oxidation with hydrogen peroxide.

This reaction sequence is also described in WO 89/2425 for preparing 2,3-difluorophenol, in which the reaction temperatures are not changed and the reaction conditions are only slightly changed:

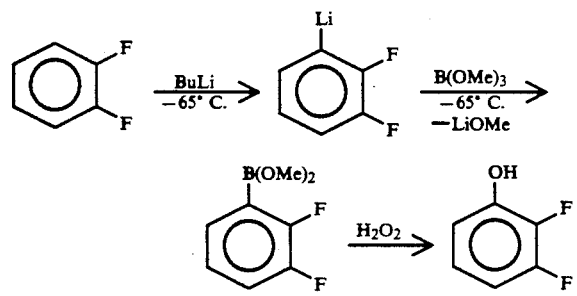

Furthermore, WO 89/2425 describes the preparation of liquid-crystalline 2,3- and 2',3'-difluoro-p-terphenylene, starting from 1,2-difluorobenzene. WO 89/8629 describes the preparation of further different liquid-crystalline compounds containing a 2,3-difluoro-1,4-phenylene group. In the processes described there, the 1,2-difluorobenzene or 1-substituted 2,3-difluorobenzene is deprotonated with a strong base, usually n-butyl-lithium, and the 2,3-difluorophenyllithium compound obtained is reacted with an electrophile.

Furthermore, the o-fluorophenyl derivatives can be prepared from the corresponding o-fluorobromobenzenes by reaction with magnesium to give o-fluorophenylmagnesium bromide, followed by derivatization (for example EP 0,238,272). In this case too, it is imperative to work at low temperatures.

The reason for the low reaction temperatures is the low stability of the o-fluorophenyllithium and -magnesium compounds. In particular 2,3-difluorophenyllithium derivatives eliminate lithium fluoride above −50° C., resulting in 1-fluoro-2,3-benzyne derivatives, which react further in an uncontrollable fashion to give unknown subsequent products.

At −50° C., the rate of the decomposition reaction of 2,3-difluorophenyllithium derivatives is still low, but at −25° C. (critical) temperature −22.5° C.) the reaction proceeds explosively, resulting in the sudden decomposition of the 2,3-difluorophenyllithium derivatives.

Such a synthesis can, of course, only be carried out on a small laboratory scale. For larger batches in production plants, this process is not possible, since the apparatus may become a potential bomb if the coolant fails.

Recent developments in the electronics industry have resulted in a substantial demand for liquid crystals containing a mono- or polyfluorinated 1,4-phenylene radical, in particular a 2,3-difluoro- or 2,6-difluoro-4-phenylene radical. Meeting this demand using existing processes is a task which is impossible to fulfill, since there is no guarantee that this low-temperature reaction can be carried out without risk on a large scale.

Thus, an object of the present invention is to find a preparation process for halogenated aromatics substituted in the ortho-position, particularly o-fluoro- or o-chlorophenyl derivatives which does not have the above-described disadvantages of the previous processes and can be carried out without risk on a large industrial scale.

Upon further study of the specification and appended claims, further objects and advantages of this invention will become apparent to those skilled in the art.

It has now been found that the desired reaction can surprisingly be made "safe" by changing the mode of addition of the reactants: if the fluoroaryl or chloroaryl derivative and the electrophile are initially introduced in an inert solvent and butyllithium or another strong base is added dropwise, the o-fluoro- or o-chloroaryl-lithium compound formed as an intermediate is trapped immediately in situ by the electrophile and cannot concentrate and thus lead to dangerous side reactions. This is a surprising finding because butyllithium and, for example, lithium diisopropylamide can themselves react with the electrophile and, accordingly, it could not be automatically expected that the o-fluorophenyl or o-chlorophenyl derivatives would be formed.

Accordingly, the invention relates to a process for the reaction of fluorinated or chlorinated aromatics with electrophiles at the ortho position relative to the fluorine atom, characterized in that a strong base is added to a mixture of the fluorinated or chlorinated aromatic and the electrophile, in particular to a process for the preparation of fluorinated or chlorinated aromatics of the formula I,

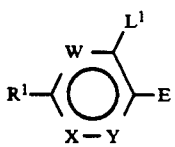

in which
L₁ and L² are each, independently of one another, F or Cl
R¹ is H, F, alkyl, alkenyl, alkoxy each having up to 18 carbon atoms or a mesogenic group,
W, X and Y are each, independently of one another, N, CH or CL²
and

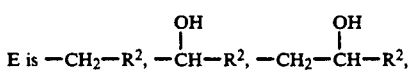

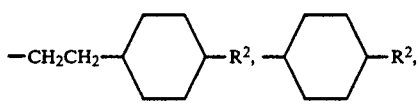

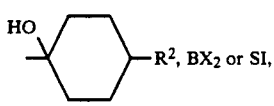

in which
R² is alkyl having 1 to 15 carbon atoms or a mesogenic radical corresponding to the group R¹,
BX₂ is a trioxatriborinane radical of the formula

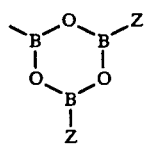

in which Z is

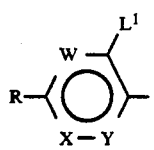

or a group of the formula —B(OR³)(OR⁴),
R³ and R⁴ are H, alkyl, alkenyl or cycloalkyl each having up to 10 carbon atoms, or taken together are an alkylenediyl group of the formula —(CH₂)ₙ— or —CH₂CHR⁸—CH₂—, in which n is 2, 3 or 4 and R⁸ is alkyl, alkoxy or alkenyl having up to 18 carbon atoms, or a mesogenic radical corresponding to the formula II, and
SI is a trihydrocarbylsilyl group of the formula —Si(R⁵)₃, in which each R⁵ is, independently of the others, an aliphatic radical having 1-6 C atoms, cycloaliphatic radical having 4-10 C atoms, araliphatic radical having 7-10 C atoms or aromatic radical having 6 to 10 C atoms.

The invention relates in particular to those processes in which R¹ is a mesogenic group of the formula II, in which $$R^0—A^1—Z^1—(—A^2—Z^2)_m— \quad\quad II$$

R⁰ is an alkyl or alkenyl radical having up to 15 carbon atoms which is unsubstituted or monosubstituted by CN, halogen or CF₃, it being possible for one or more CH₂ groups in these radicals to be each replaced, independently of one another, by —S—, —O—, —CO—, —CO—O—, —O—CO— or —O—CO—O— such that S and/or O atoms are not linked directly to one another.

Z¹ and Z² are each, independently of one another, —CH₂CH₂—, —C≡C—, —CH₂O—, —CO—O—, —O—CO—, —CH=N—, —N=CH—, —CH₂S—, —SCH₂—, a single bond or an alkylene group having 3 to 6 carbon atoms. in which one CH₂ group can also be replaced by —O—, —CO—O—, —O—CO—, —CHhalogen- or —CHCN—, and A¹ and A² are each, independently of one another,
(a) a trans-1,4-cyclohexylene radical, in which one or more non-adjacent CH₂ groups can also be replaced by —O— and/or —S—,
(b) a 1,4-phenylene radical, in which one or two CH groups can also be replaced by N,
(c) a radical from the group comprising 1,3-cyclobutylene, 1,3-bicyclo[1.1.1]pentylene, 1,4-cyclohexenylene, 1,4-bicyclo[2.2.2]-octylene, piperidine-1,4-diyl, naphthalene-2,6-diyl, decahydronaphthalene-2,6-diyl and 1,2,3,4-tetrahydronaphthalene-2,6-diyl,
it being possible for the radicals (a) and (b) to be substituted by CN or halogen, and
m is 0, 1 or 2.

When R⁵ is aliphatic, preferred is 1–4 C atoms, in particular methyl, ethyl or tert-butyl; cycloaliphatic, particularly preferred is 5–7 C atoms; araliphatic, particularly preferred is benzyl; aromatic, particularly preferred is phenyl or tolyl.

The reaction of the fluorinated or chlorinated aromatics with the corresponding borates usually first results in the cyclic trimers of the corresponding o-fluoroarylboronic or o-chloroarylboronic acid of the formula IB′

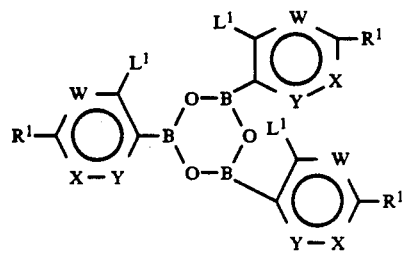

which, however, are converted into the corresponding compounds of the formula IB by hydrolysis or alcoholysis.

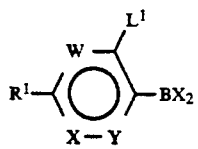
IB

Furthermore, the invention relates to the use of the o-fluoro- or chloroarylboronic acids or esters thereof of the formula IB, prepared by the process according to the invention, for the preparation of the corresponding o-fluoro- or chlorophenols, in particular of 2,3-dichlorophenol, 2,3-dichlorohydroquinone, 2,3-difluorophenol and 2,3-difluorohydroquinone, by oxidative hydrolysis, to their use as coupling components in transition-metal-catalyzed cross-coupling with halogen or perfluoroalkyl sulfone compounds, and for the preparation of the corresponding o-fluoro- or chlorohaloaromatics by halogenation.

The o-fluoro- and chlorophenylboronic acids and esters thereof the formula IB are partly known, partly new. The new ones of these compounds are also provided by the present invention, in particular the compounds of the formulae IB1 and IB2,

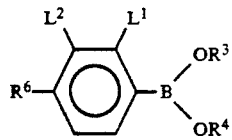
IB1 in which $L^1$ and $L^2$, $R^3$ and $R^4$ are as defined above, and $R^6$ is F, alkyl having 1-15 C atoms, $C_1$-$C_{15}$-alkyl

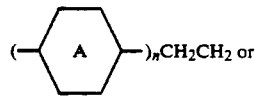

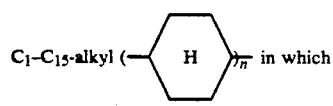 in which

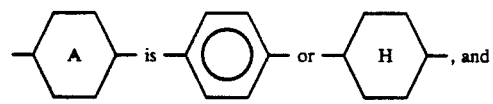, and n is 1 or 2,

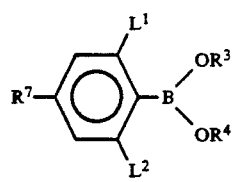
IB2 in which $L^1$, $L^2$, $R^3$ and $R^4$ are as defined, and
$R^7$ is H, F, alkoxy each having up to 18 carbon atoms or a mesogenic group corresponding to the formula II, and trimeric anhydrides thereof.

When $R^6$ is an alkyl, preferred is 1-10 C atoms, in particular 2-9 C atoms.

The o-fluoro- and o-chloroaryl derivatives prepared by the process according to the invention comprise mono-, di-, tri-, tetra- and penta-fluoro- and -chlorophenyl derivatives.

In addition, 2-fluoro- and 2-chloropyridin-3-yl derivatives can also be prepared by the process according to the invention. Whether or not further substituents are present on the aromatic ring apart from the fluoro and chloro substituents, is not critical for carrying out the process according to the invention. Examples of further substituents are alkyl, alkenyl or alkoxy groups, bromine or mesogenic groups. In addition, the fluorinated and chlorinated aromatic rings can also be constituents of fused ring systems, such as, for example, of naphthalenes, di- and tetrahydronaphthalenes or of 2,3,4,5-tetrahydro-1H-3-benzazepine derivatives.

Hereinafter, for the sake of simplicity, Phe is a 1,4-phenylene group, in which one or two CH groups can also be replaced by N, it being possible for a 1,4-phenylene group also to be substituted by one or two halogen atoms, ArL is a fluorinated or chlorinated 1,4-phenylene group of the formula

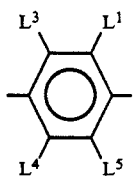

in which $L^1$ is F or Cl, and $L^3$, $L^4$ and $L^5$ are each, independently of one another, H, Cl or F.

Cy is a trans-1,4-cyclohexylene radical, in which one or more non-adjacent CH, groups can also be replaced by —O—.

E is a group introduced by the reaction according to the invention.

$BX_2$ is a trioxatriborinane radical of the formula

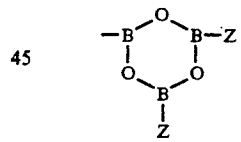

in which
Z is the o-fluoro- or o-chlorophenyl group defined in each case,
or
a group of the formula $B(OR^3)(OR^4)$,
in which $R^3$ and $R^4$ are as defined, $R^3$ and $R^4$ being preferably identical and having the meaning of hydrogen, methyl or isopropyl.

The compounds of the formula I prepared by the process according to the invention comprise those of the formulae Ia to Ic

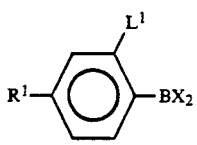
Ia

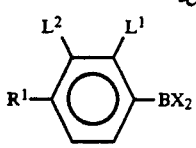  Ib

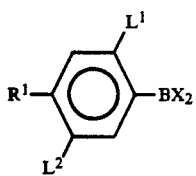  Ic

Preferred alkylation and hydroxyalkalation reagents are the compounds of the formula IIIa to IIIf:

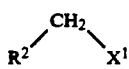  IIIa $R^2$—CHO  IIIb

  IIIc

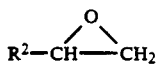

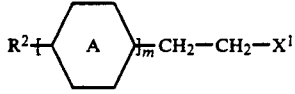  IIId

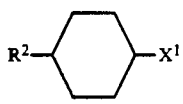  IIIe

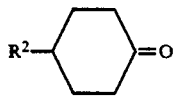  IIIf in which $R^2$ is alkyl having 1 to 15 carbon atoms or a mesogenic group corresponding to the formula II,

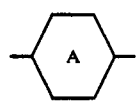

is

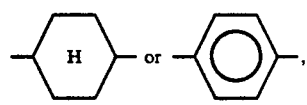

m is 1 or 2 and $X^1$ is Cl, Br, iodine or a perfluoroalkylsulfonyloxy group wherein the alkyl group has 1–10 C atoms, in particular 1–4 C atoms.

Silylating reagents are the compounds of the formula IIIg, SI-L, in which SI is as defined and L is a leaving group, in particular compounds of the formulae IIIga to IIIgh:

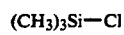  IIIga

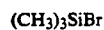  IIIgb

| | |
|---|---|
| $(CH_3)_3SiI$ | IIIgc |
| $(CH_3)_3SiOSO_2CF_3$ | IIIgd |
| $(CH_3)_2(tert\text{-}C_4H_9)SiCl$ | IIIge |
| $(C_6H_5)_2(tert\text{-}C_4H_9)SiCl$ | IIIgf |
| $(C_2H_5)_3SiCl$ | IIIgg |
| $(I\text{—}C_3H_7)_3SiCl$ | IIIgh |

For the preparation of the compounds of the formula I in which E is $B(OR^3)(OR^4)$, trialkyl borates or analogs thereof of the formula IIIh, $B(OR^3)(OR^4)(Oalkyl)$, in particular $B(Oalkyl)_3$, are suitable. The O alkyl group has 1–10 C atoms preferably 1–4 C atoms, and is most preferably a methoxy group.

The compounds of the formula I prepared by the process according to the invention comprise those of the formula Ia to Ig Ia Ib Ic Id Ie If

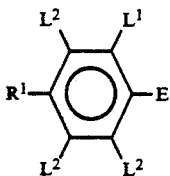

Ig

Of these, the compounds of the formulae Ia, Ib, Id and Ig are particularly preferred. In the compounds mentioned of the formulae Ia to Ig, $L^1$ and $L^2$ are preferably F, $R^1$ is preferably H, alkyl or alkoxy each having 1 to 12 carbon atoms or a mesogenic radical, particular preference in the process according to the invention being given to the compounds of the formula Ib, in which $R^1$ is H or alkoxy having 1 to 12, particular 2 to 4, carbon atoms. These suitable in particular as intermediates for the preparation of liquid crystals containing a 2,3-difluoro-1,4-phenylene or 2,3-difluoro-1,4-phenyleneoxy structural unit. The compounds of the formula I containing a mesogenic radical of the formula II accordingly comprise the compounds of the formula I1 to I13:

| | |
|---|---|
| $R^0-A^1-ArL-E$ | I1 |
| $R^0-A^1-Z^1-ArL-E$ | I2 |
| $R^0-A^1-A^2-ArL-E$ | I3 |
| $R^0-A^1-A^2-Z^2-ArL-E$ | I4 |
| $R^0-A^1-Z^1-A^2-ArL-E$ | I5 |
| $R^0-A^1-Z^1-A^2-Z^2-ArL-E$ | I6 |
| $R^0-A^1-A^2-A^2-ArL-E$ | I7 |
| $R^0-A^1-Z^1-A^2-A^2-ArL-E$ | I8 |
| $R^0-A^1-A^2-Z^2-A^2-ArL-E$ | I9 |
| $R^0-A^1-A^2-A^2-Z^2-ArL-E$ | I10 |
| $R^0-A^1-Z^1-A^2-Z^2-A^2-ArL-E$ | I11 |
| $R^0-A^1-Z^1-A^2-A^2-Z^2-ArL-E$ | I12 |
| $R^0-A^1-A^2-Z^2-A^2-Z^2-ArL-E$ | I13 |

Of these, the compounds of the formulae I1, I2, I3, I4 and I7 are particularly preferred, in particular those in which ArL is a radical of the formula

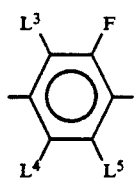

and $L^3$, $L^4$, $L^5$ are H or F.

Of the compounds of the formula I1, those of the formulae I1a to I1c are particularly preferred.

| | |
|---|---|
| Alkyl—Phe—ArL—E | I1a |
| Alkyl—Cyc—ArL—E | I1b |
| Alkoxy—Phe—ArL—E | I1c |

Of the compounds of the formula I2, those of the formulae I2a to I2i are particularly preferred.

| | |
|---|---|
| Alkyl—Phe—CH$_2$CH$_2$—ArL—E | I2a |
| Alkyl—Phe—CH$_2$O—ArL—E | I2b |
| Alkyl—Phe—C≡C—ArL—E | I2c |
| Alkoxy—Phe—C≡C—ArL—E | I2d |
| Alkoxy—Phe—CH$_2$O—ArL—E | I2e |
| Alkoxy—Phe—CH$_2$CH$_2$—ArL—E | I2f |
| Alkyl—Cyc—CH$_2$CH$_2$—ArL—E | I2g |
| Alkyl—Cyc—CH$_2$O—ArL—E | I2h |
| Alkyl—Cyc—C≡C—ArL—E | I2i |

In the preferred compounds of the formulae above and below, $R^1$ is an alkyl group preferably having 1 to 10 carbon atoms, or an alkoxy or an alkenyl group each preferably having 1 to 10 carbon atoms.

$L^1$ is preferably F, $L^2$ is preferably F and, in the case where $L^1$ is Cl, preferably Cl.

Particularly preferred alkyl groups are hexyl, pentyl, butyl, i-butyl, propyl, i-propyl, methyl and ethyl, in particular methyl; particularly preferred alkoxy groups are hexoxy, pentoxy, i-butoxy, propoxy, i-propoxy, methoxy and ethoxy, in particular methoxy; particularly preferred alkenyl groups are hexenyl, pentenyl, butenyl and allyl.

In the preferred compounds of the formulae above and below, the alkyl radicals in which a CH$_2$ group (alkoxy or oxaalkyl) can also be replaced by an O atom can be straight-chain or branched. Preferably, they have 2, 3, 4, 5, 6, 7, 8, 9 or 10 carbon atoms and accordingly are preferably ethyl, propyl, butyl, pentyl, hexyl, heptyl, octyl, nonyl, decyl, propoxy, ethoxy, butoxy, pentoxy, hexoxy, heptoxy, octoxy, nonoxy or decoxy, furthermore also undecyl, dodecyl, undecoxy, dodecoxy, 2-oxapropyl (=2-methoxymethyl), 2- (=ethoxymethyl) or 3-oxabutyl (=2-methoxypentyl), 2-, 3- or 4-oxapentyl, 2-, 3-, 4- or 5-oxahexyl, or 2-, 3-, 4-, 5- or 6-oxaheptyl.

$A^1$ and $A^2$ are preferably Cyc or Phe. In the compounds of the formulae above and below, Phe is preferably a 1,4-phenylene (Ph), a 1,4-phenylene group mono- or disubstituted by F or CN (PheX), a pyrimidin-2,5-diyl (Pyr), a pyridin-2,5-diyl (Pyn), a pyrazin-3,6-diyl or a pyridazin-2,5-diyl group, is particular preferably Ph, PheX, Pyr or Pyn. The compounds prepared by the process according to the invention preferably contain not more than one 1,4-phenylene group, in which one or two CH groups are replaced by N. Cyc is preferably a 1,4-cyclohexylene group. However, preference is given in particular to compounds of the formula I in which one of the groups $A^1$ and $A^2$ is a 1,4-cyclohexylene group substituted in the 1 or 4 position by CN and the nitrile group is in the axial position, i.e., the group $A^1$ or $A^2$ has the following configuration:

Particular preference is given to compounds of the formula I and the subformulae above containing a grouping —Phe-Phe—. —Phe-Phe— is preferably —Ph-Ph—, Pyr-Phe or Ph-Pyn. Particular preference is given to the groups

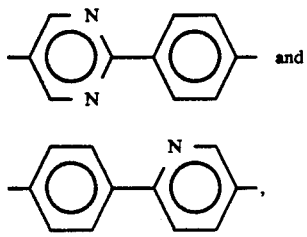

and furthermore to 4,4'-biphenylyl which is unsubstituted or mono- or polysubstituted by fluorine.

In particular, preference is given to compounds of the formula I and of the subformulae below containing a 2,3-difluoro-1,4-phenylene group.

The groups $Z^1$ and $Z^2$ are each, independently of one another, preferably a single bond, secondly preferably —C≡C— or —CH$_2$CH$_2$— groups. In particular, preference is given to compounds of the formula I in which the group $Z^1$ is —CH$_2$CH$_2$—.

Compounds of the formulae above and below having branched wing groups $R^1$ can be of importance. Branched groups of this type usually contain not more than two chain branchings. $R^1$ is preferably a straight-chain group or a branched group having not more than one chain branching.

Preferred branched radicals are isopropyl, 2-butyl (=1-methylpropyl), isobutyl (=2-methylpropyl), tert.-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl.

The radical $R^1$ can also be an optically active organic radical containing an asymmetric carbon atom. Preferably, the asymmetric carbon atom is then linked to two differently substituted carbon atoms, an H atom and a substituent selected from the group comprising fluorine, alkyl or alkoxy each having 1 to 5 carbon atoms and CN. The optically active organic radical $R^1$ preferably has the formula

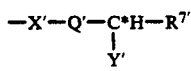

in which
X' is —O—, —S— or a single bond,
Q' is alkylene having 1 to 5 carbon atoms, in which one CH$_2$ group not linked to X' can also be replaced by —O—, or a single bond,
Y' is CN, F, CF$_3$, methyl or methoxy, and
$R^{7'}$ is an alkyl group different from Y' and having 1 to 15 carbon atoms, in which one or two non-adjacent CH$_2$ groups can also be replaced by —S—, —O—.

X' is preferably a single bond.

Q' is preferably —CH$_2$—, —CH$_2$CH$_2$—, —CH$_2$CH$_2$CH$_2$— or a single bond, in particular preferably a single bond.

Y' is preferably CH$_3$, —CN or F, in particular preferably CN or F.

$R^{7'}$ is preferably straight-chain or branched alkyl or alkoxy having 1 to 10, in particular 1 to 7, carbon atoms.

Of the compounds of the formula I and Ia to Ig, those are preferred in which at least one of the radicals contained therein has one of the preferred meanings mentioned.

The compounds prepared by the process according to the invention of the formula IA

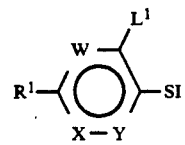

are new and comprise those of the formulae IAa to IAg

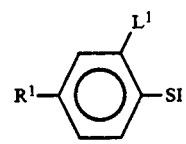
IAa

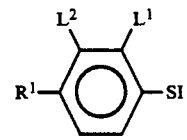
IAb

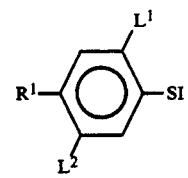
IAc

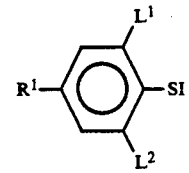
IAd

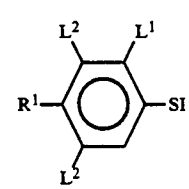
IAe

-continued

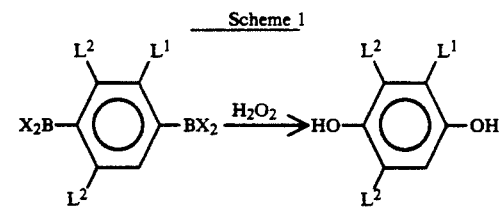

IAf ing difluorohydroquinone, which in turn can be used for the synthesis of liquid crystals (for example according to Scheme 1).

Scheme 1

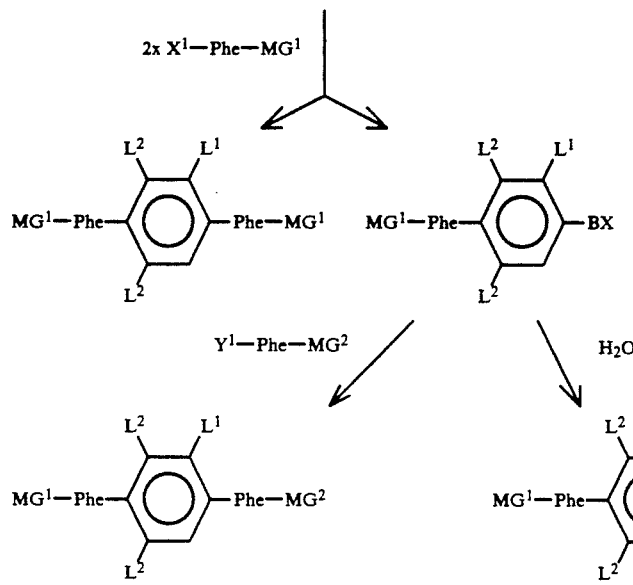

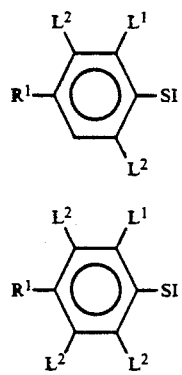

IAg

The new compounds of the formula IA are also provided by the present invention. Of these, the compounds of the formulae IAa, IAb, IAd and IAg are particularly preferred.

In addition, the process according to the invention is suitable for preparing new difluoro-1,4-phenylenediboronic acids or anhydrides thereof the formula IB3,

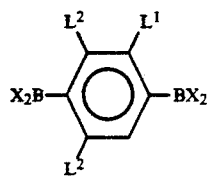

IB3 in which $L^1$ is F and one of the radicals $L^2$ is F or $L^1$ is Cl and one of the radicals $L^2$ is Cl. These are highly suitable for preparing symmetrical liquid crystals by transition-metal-catalyzed cross-coupling or for prepar- $MG^1$, $MG^2$ are mesogenic groups corresponding to the radical of the formula II $X^1$, $Y^1$ is a halogen or perfluoroalkylsulfonyloxy, preferably iodine, bromine or triluromethylsulfonyloxy.

The new difluoro- and -chlorophenylboronic acids of the formulae IB1 and IB2 are furthermore suitable for preparing new liquid-crystalline difluoro- or -chlorophenyldioxaborinanes of the formulae IB1a and IB2a

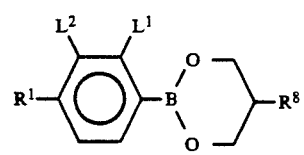

IB1a

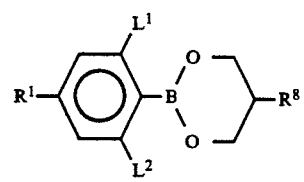

IB2a in which R' is as defined, and $R^8$ is alkyl, alkenyl or alkoxy having up to 18 carbon atoms or a mesogenic group corresponding to the formula II.

The new difluoro- and -chlorophenyldioxaborinanes of the formula IB1a and IB2a are also provided by the invention.

An aromatic is an organic compound containing one or more unsaturated rings and having 5-10 carbon atoms, the rings may be fused or covalently bonded. It also includes unsaturated heterocyclic ring structures with at least one N, S and/or O ring/atom. Preferably, the halogenated aromatic is a compound with a chlorinated or fluorinated benzene, pyridine, pyrimidine or pyridazine group in which there is a hydrogen atom in the o-position relative to the halogen atom.

The compounds of the formula IV

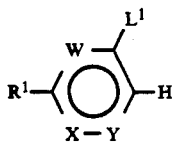

in which R$^1$, L, W, X and Y are as defined, which are preferred as starting materials, are known or are prepared by methods known per se, such as described in the literature (for example in the standard works such as HoubenWeyl, Methoden der organischen Chemie (Methods of organic chemistry), Georg-Thieme-Verlag, Stuttgart), under reaction conditions known and suitable for the reactions mentioned. Variants known per se but not mentioned here in more detail can also be used.

The reaction procedure of the process according to the invention is simple and comprises reacting the starting materials at temperatures of $-100°$ to $100°$ C., preferably $-40°$ to $40°$ C., in particular $0°$ to $35°$ C., and at elevated or reduced pressure, preferably at atmospheric pressure.

A significant advantage of the process according to the invention compared with that known from the prior, art is the fact that it is not necessary to work at low temperatures ($-100°$ to $-65°$ C.), in order to prevent explosive decomposition of the o-fluoro- or o-chlorophenyllithium at elevated temperatures, since this compound is only formed in situ and is always trapped by the alkylating or hydroxyalkylating agent present.

Advantageously, the fluorinated aromatic is initially introduced in a mixture with the electrophile in an inert solvent, and the strong base is added. The reaction can be carried out in the absence or, advantageously, in the presence of an inert solvent, suitable solvents being the conventional solvents for reactions with strong bases, for example ethers, such as diethyl ether, tetrahydrofuran or methyl tert.-butyl ether, hydrocarbons, such as pentane, hexane, heptane, benzene, toluene, xylene or cyclohexane or mixtures of the solvents mentioned. It is also possible to add cosolvents, such as, for example, hexamethylphosphoric triamide (HMPT), tetramethylethylenediamine (TMEDA), dimethylpropyleneurea (DMPU) or crown ethers, such as 18-crown-6, to these solvents. The amount of solvent is not critical, it being in general possible to use 100 to 1000 g of solvent per mole of fluorinated aromatic compound.

An electrophile is an electron pair acceptor which seeks the electron rich center of an organic compound. Suitable electrophiles include alkylating or hydroxylating agents, silylating agents and trialkyl borates.

Suitable electrophiles are the compounds mentioned of the formulae IIIa to IIIf, preferably n-alkyl halides having 1 to 16 carbon atoms, in particular n-alkyl bromides and iodides, such as, for example, methyl bromide, ethyl bromide, propyl bromide, butyl bromide, pentyl bromide, hexyl bromide, heptyl bromide, octyl bromide or nonyl bromide or methyl iodide, ethyl iodide, propyl iodide, butyl iodide, pentyl iodide, hexyl iodide, heptyl iodide, octyl iodide or nonyl iodide, n-alkanals having 2 to 16 carbon atoms, in particular acetaldehyde, propionaldehyde, butyraldehyde, pentanal, hexanal, heptanal, octanal or nonanal, oxiranes, such as, for example, oxirane, 2-methyloxirane, 2-ethyloxirane, 2-propyloxirane, 2-butyloxirane, 2-pentyloxirane, 2-hexyloxirane or 2-heptyloxirane.

Suitable silylating agents are the compounds of the formulae IIIg, preferably trialkylsilyl halides in which the alkyl groups are straight-chain or branched and have 1 to 8 carbon atoms, in particular the compounds of the formulae IIIga to IIIgf.

Suitable trialkyl borates are usually compounds of the formula B(OR$^3$)$_2$(OR$^1$), preferably B(OR$^3$)$_3$, in which R$^3$ is methyl, ethyl, propyl, butyl or isopropyl, in particular methyl or isopropyl.

The type of the strong base to be used depends on the fluorinated aromatics used. Usually, the strong bases customary in organic chemistry are used (for example House: Modern Synthetic Reactions 2nd Ed., Benjamin 1972, p. 547). Particularly suitable strong bases are alkali metals, such as lithium, sodium or potassium, alkali metal hydrides, such as lithium hydride, sodium hydride or potassium hydride, alkaline earth metal hydrides, such as calcium hydride, organometallic compounds, such as n-butyllithium, sec.-butyllithium, tert.-butyllithium, methyllithium, ethyllithium or phenyllithium, in particular n-butyllithium, strong amide bases, such as sodium amide, potassium amide, lithium diisopropylamide, lithium cyclohexylisopropylamide, lithium dicyclohexylamide, 2,2,6,6-tetramethylpiperidin-1-yllithium, lithium hexamethyldisilazane or potassium hexamethyldisilazane, in particular lithium diisopropylamide.

A further advantage of the process according to the invention is that it is at any time safe to interrupt and resume later, since only unreactive compounds, such as the fluorinated aromatic, the alkylating or hydroxyalkylating agent, metal alcoholate and the o-fluoro- or chloroaryl derivative, are present during the dropwise addition of the base.

In a preferred embodiment of the process according to the invention, the fluoro- or chloroaromatic is initially introduced together with about 10-80%, in particular 15-25%, of the electrophile to be used in an inert solvent, preferably tetrahydrofuran, and the base, preferably lithium diisopropylamide, is added simultaneously in an inert solvent under an inert gas atmosphere together with the remaining amount of the electrophile (20-90%, preferably 75 to 85%).

As a rule, 0.8 to 2.2 mol, preferably 1.2 to 1.8 mol of base and 0.8 to 1.5 mol, preferably 1.0 to 1.3 mol of electrophile are required for 1 mole of the fluoroaromatic to be deprotonated.

Workup of the reaction mixture and isolation of the products is carried out in the usual manner, for example by pouring the reaction mixture into water and/or onto ice or into dilute acid and separating off the aqueous phase, followed by recovering the o-fluoro- or chloroarylboronic acid derivative by distillation or crystallization.

However, not only the trimeric anhydrides of the o-fluoroarylboronic acids but also the free boronic acids can also be hydrolyzed to the corresponding o-fluoroor chlorophenols without any purification step by reaction with $H_2O_2$.

Surprisingly, the process according to the invention makes it possible to prepare the o-fluoro- or chloroaryl derivatives, which are valuable intermediates, for example for liquid crystals, auxiliaries, crop protection agents and pharmaceuticals, in a simple manner, without risk, on a larger scale and in higher yields compared with the prior art.

The fluorinated and chlorinated arylsilanes according to the invention of the formula IA can be reacted, for example according to Scheme 1, to give o-fluorinated and chlorinated phenols and phenylboronic acids, which can be converted to liquid-crystalline products by transition-metal-catalyzed cross-coupling according to WO 89/2425.

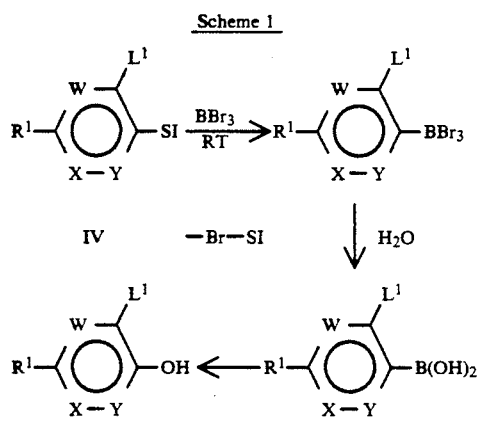

Furthermore, the arylsilanes according to the invention of the formula IA can be used to prepare o-fluorinated halogenzene derivatives according to Scheme 2:

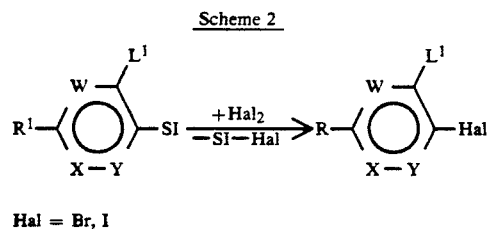

Moreover, the compounds according to the invention of the formula IA can be used to prepare o-fluorinated alkyl- and acylbenzene derivatives according to Scheme 3:

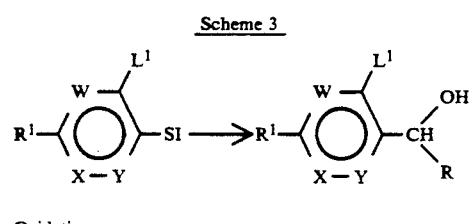

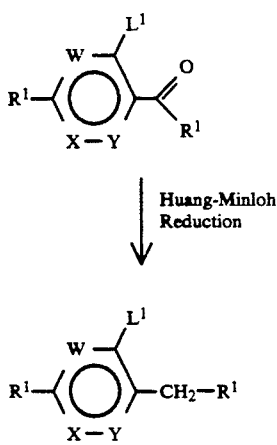

The $^1H$ nuclear magnetic resonance spectra were recorded using a 200 MHz spectrometer from Bruker.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 40 02 896.8, filed Feb. 1, 1990, P 42 01 308.9, filed Jan. 20, 1992, and Europe 0 440 082 A2, published Aug. 7, 1991, are hereby incorporated by reference.

EXAMPLES

EXAMPLE 1

Preparation of 1-(4'-pentylbiphenyl-4-yl)-2-(3,5-di-fluoro-4-propyl-phenyl)ethane A solution of lithium diisopropylamide (0.02 mol) in THF/hexane, prepared from 0.02 mol of diisopropylamine in 25 ml of THF and 12.5 ml of a 1.6-molar solution of n-butyllithium in hexane, is added dropwise at 25° C. to a mixture of 0.02 mol of 1-(4'-pentylbiphenyl-4-yl)-2-(3,5-difluorophenyl)ethane, 0.02 mol of N,N-dimethylpropyleneurea, 0.02 mol of 1-iodopropane and 25 ml of THF. After stirring at room temperature for 1.5 hours, the reaction mixture is poured into water, the phases are separated, and the aqueous phase is extracted with 2×50 ml of methylene chloride. Drying over magnesium sulfate, evaporation of the solvent and chromatography give the pure product.

The following are prepared analogously:

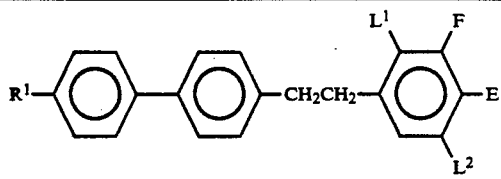
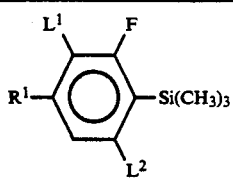

| R¹ | L¹ | L² | E |
|---|---|---|---|
| C₅H₁₁ | H | F | C₅H₁₁ |
| C₅H₁₁ | F | H | C₃H₇ |
| C₅H₁₁ | F | H | C₅H₁₁ |

| R¹ | L¹ | L² |
|---|---|---|
| C₂H₅O | F | H |
| C₂H₅O | H | F |
| C₂H₁₁ | H | F |

EXAMPLE 2

Preparation of 2-(4'-propylbicyclohexyl-4-yl)-1-(2,6-difluoropyridine-3-yl)ethane A solution of 0.02 mol of lithium diisopropylamide in THF/hexane (prepared analogously to Example 1) is added dropwise at 25° C. to a mixture of 0.2 mol of 2,6-difluoropyridine, 0.02 mol of N,N-dimethylethyleneurea, 0.02 mol of 2-(4'-propylbicyclohexyl-4-yl)-1-iodoethane and 25 ml of THF. Stirring for 1.5 hours and workup as described in Example 1 give the pure product.

The following are prepared analogously:

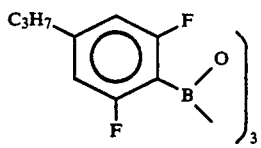

| R¹ | L² | Y | R² |
|---|---|---|---|
| F₃C | H | CH | C₃H₇ K 80 N 103.8 I |
| C₅H₁₁ | H | CF | C₃H₇ |
| C₅H₁₁ | F | CH | C₃H₇ |

EXAMPLE 3

Preparation of 2,3-difluorotrimethylsilylbenzene 12.5 ml of a 1.6-molar solution of n-butyllithium in hexane is added dropwise at 0° C. to a mixture of 0.02 mol of 1,2-difluorobenzene, 0.02 mol of trimethylchlorosilane and 25 ml of THF. After stirring at room temperature for 1.5 hours, the reaction mixture is poured into water, the phases are separated, and the aqueous phase is extracted with 2×50 ml of methylene chloride. Drying over magnesium sulfate, evaporation of the solvent and chromatography give the pure product.

The following are prepared analogously:

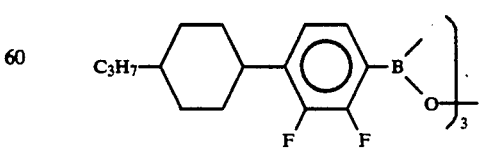

| R¹ | L¹ | L² |
|---|---|---|
| H | H | F |
| C₅H₁₁ | F | H |

EXAMPLE 4

700 g of 1,2-difluorobenzene, 1.2 l of tetrahydrofuran and 168 ml of trimethyl borate are initially introduced into a 20 l three-necked flask under nitrogen and with stirring. 658 ml of trimethyl borate and 6.58 l of a lithium diisopropylamide/tetrahydrofuran solution (prepared from 1.09 l of diisopropylamine, 4.49 l of 15% butyllithium in hexane and 1 l of absolute tetrahydrofuran) are simultaneously added dropwise over a period of 2 hours, during which the temperature is maintained between 19° and 23° C. by occasional water cooling. Stirring is continued for 30 minutes, and 800 ml of glacial acetic acid and 1600 g of 50% sulfuric acid are run in in succession, the mixture is stirred for 30 minutes and allowed to settle. The aqueous phase is extracted twice with 250 ml each of methyl tert.-butyl ether, and the combined organic phases are washed twice with 250 ml each of saturated sodium bicarbonate solution. After drying over sodium sulfate and evaporation at 50°-70° C. in vacuo, 717 g of the trimeric anhydride of 2,3-difluorophenylboronic acid remain (molecular weight: 420) mass spectrum (MS): 421 (molecular peak), 325, 279, 253, 235

The following are prepared analogously:

4-n-Propyl-2,6-difluorophenylboronic anhydride (MW: 489)

MS: 490,325,163

4-(4-Propyl-)cyclohexyl)-2,3-difluorophenylboronic anhydride (MW: 735)

MS: 736,489,245

4-Propyl-2,3-difluorophenylboronic anhydride (MW: 489)

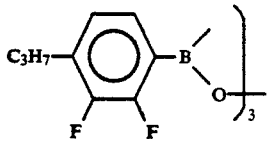

MS: 490,325,163

4-(4-Ethyl-)phenyl-2,3-difluorophenylboronic anhydride (MW: 675)

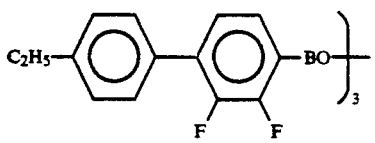

MS: 676,449,225

4-(2-(4-(4-Propyl-)cyclohexyl-)cyclohexyl-)ethyl-2,3-difluorophenylboronic anhydride (MW: 1065)

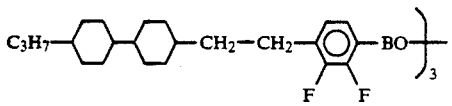

MS: 1066,709,335

4-Ethoxy-2,3-difluorophenylboronic anhydride (MW: 495)

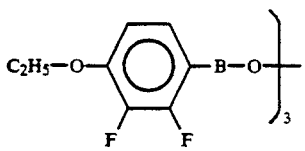

MS: 496,329,165

EXAMPLE 5

10 g of trimeric 2,3-difluorophenylboronic anhydride are prepared according to Example 1 from 1,2-difluorobenzene, lithium diisopropylamide and trimethyl borate. The anhydride is dissolved in 200 ml of boiling water. The hot solution is filtered, and the filtrate is allowed to cool slowly to room temperature. The solid is separated off and dried to give 2,3-difluorophenylboronic acid having a melting point of 89° C.

$^1$H NMR (CDCl$_3$/TMS) : δ=5.2 (2H), 7.1–7.4 (2H), 7.6 (1H).

EXAMPLE 6

Dimethyl 4-propyl-2,6-difluorophenylboronate 4.9 g of 4-propyl-2,6-difluorophenylboronic anhydride (prepared according to Example 1) are dissolved in 100 ml of methanol, 0.3 g of p-toluenesulfonic acid and 5 g of molecular sieve 4 Å are added, and the mixture is refluxed for 1 hour. 1 g of basic alumina is added, the mixture is filtered, the filtrate is evaporated to give a residue of 5.4 g of dimethyl 4-propyl-2,6-difluorophenylboronate.

$^1$H NMR (CDCl$_3$/TMS): δ=6.95 (2H), 2.9 (6H) ppm

EXAMPLE 7

4-(4-Propyl-2,6-difluorophenyl)-2,6-dioxaborinane 4.9 g of 4-propyl-2,6-difluorophenylboronic anhydride (prepared according to Example 1) are dissolved in 200 ml of toluene, and 3 g of 1,3-propanediol and 0.3 g of p-toluenesulfonic acid and 5 g of molecular sieve 4 Å are added. The mixture is heated at 60° C. for 3 hours, cooled and filtered through a chromatography column filled with 20 g of basic alumina. After additional elution using toluene, the substance-carrying fractions are evaporated, giving the pure product.

$^1$H NMR (CDCl$_3$/TMS): δ=6.95 (2H), 2.9 (6H) ppm

The following are prepared analogously:

1-(4-Propyl-2,6-difluorophenyl)-4-ethyl-2,6-dioxaborinane
1-(4-Propyl-2,6-difluorophenyl)-4-propyl-2,6-dioxaborinane
1-(4-Propyl-2,6-difluorophenyl)-4-butyl-2,6-dioxaborinane
1-(4-Propyl-2,6-difluorophenyl)-4-pentyl-2,6-dioxaborinane
1-(4-Propyl-2,6-difluorophenyl)-4-hexyl-2,6-dioxaborinane
1-(4-Propyl-2,6-difluorophenyl)-4-heptyl-2,6-dioxaborinane
1-(4-Pentyl-2,6-difluorophenyl)-4-ethyl-2,6-dioxaborinane
1-(4-Pentyl-2,6-difluorophenyl)-4-propyl-2,6-dioxaborinane
1-(4-Pentyl-2,6-difluorophenyl)-4-butyl-2,6-dioxaborinane
1-(4-Pentyl-2,6-difluorophenyl)-4-pentyl-2,6-dioxaborinane
1-(4-Pentyl-2,6-difluorophenyl)-4-hexyl-2,6-dioxaborinane
1-(4-Pentyl-2,6-difluorophenyl)-4-heptyl-2,6-dioxaborinane
1-(4-Ethoxy-2,3-difluorophenyl)-4-ethyl-2,6-dioxaborinane
1-(4-Ethoxy-2,3-difluorophenyl)-4-propyl-2,6-dioxaborinane
1-(4-Ethoxy-2,3-difluorophenyl)-4-butyl-2,6-dioxaborinane
1-(4-Ethoxy-2,3-difluorophenyl)-4-pentyl-2,6-dioxaborinane
1-(4-Ethoxy-2,3-difluorophenyl)-4-hexyl-2,6-dioxaborinane
1-(4-Ethoxy-2,3-difluorophenyl)-4-heptyl-2,6-dioxaborinane
1-(4-Propyl-2,3-difluorophenyl)-4-ethyl-2,6-dioxaborinane
1-(4-Propyl-2,3-difluorophenyl)-4-propyl-2,6-dioxaborinane
1-(4-Propyl-2,3-difluorophenyl)-4-butyl-2,6-dioxaborinane
1-(4-Propyl-2,3-difluorophenyl)-4-pentyl-2,6-dioxaborinane
1-(4-Propyl-2,3-difluorophenyl)-4-hexyl-2,6-dioxaborinane
1-(4-Propyl-2,3-difluorophenyl)-4-heptyl-2,6-dioxaborinane

EXAMPLE 8

Materials used:

| | | |
|---|---|---|
| 14.7 g | of 1,2-dichlorobenzene | 100 mmol |
| 11.4 g | of trimethyl borate (TMB) | 110 mmol |
| 55 ml | of lithium diisopropylamide solution (LDA) | 110 mmol |
| 50 ml | of tetrahydrofuran (THF) | |
| 6.5 ml | of acetic acid | |
| 3.1 ml | of sulfuric acid | |
| 13.5 ml | of 30% hydrogen peroxide | |

Dichlorobenzene is initially introduced in 40 ml of THF, and 2 ml of TMB are added. The remaining TMB is diluted with 10 ml of THF and added dropwise simultaneously with the LDA solution. The reaction temperature was maintained at 15°–25° C.

After an afterreaction time of ¼ hour, 6.5 ml of acetic acid are added. 3.1 ml of sulfuric acid are then added at the same temperature with cooling.

13.5 ml of hydrogen peroxide are added dropwise at 35° C. over a period of ½ hour. The mixture is refluxed for 3 hours.

The next day, 50 ml of water and 50 ml of methyl-tert.-butyl ether (MTB) were added, and the mixture was acidified with hydrochloric acid. The organic phase was extracted with water and evaporated in vacuo.

The crude product was dissolved in MTB, water was added, and the mixture was made alkaline (pH 11) with sodium hydroxide solution. The aqueous phase was separated off and washed with water. The organic phases were discarded. The aqueous phase was acidified and extracted with MTB ether. The organic phase was concentrated to give a residue of 9 g (=55% of theory) of 2,3-dichlorophenol MS: 162, 126, 98, 63

Use Example 1

Preparation of 4-ethoxy-2,3-difluoro-4'-pentylbiphenyl

A solution of 4-ethoxy-2,3-difluorophenylboronic anhydride (3.7 g) in ethanol is added to a solution of 3.8 g of p-pentylbromobenzene and 0.16 g of tetrakis(triphenylphosphino)palladium (0) in a solvent mixture of benzene (20 ml) and 2M-Na$_2$CO$_3$ (20 ml) at 20° C. The mixture is heated at 95° C. for 30 hours. After cooling, the mixture is stirred at room temperature with 30% H$_2$O$_2$ (2 ml) for 1 hour. Customary workup and recrystallization give the pure product. The 4-ethoxy-2,3-difluoro-4'-pentylbiphenyl can be used as an intermediate in the preparation of liquid crystal compounds as discussed in WO 89/08637, the disclosure of which is hereby incorporated by reference.

Use Example 2

Preparation of 2,3-difluorophenol 4.4 g of the 2,3-difluorophenylboronic anhydride prepared according to Example 1 are reacted with 25 ml of 30% H$_2$O$_2$ by the method of M. F. Hawthorne, J. Org. Chem. (1957) 22, 1001. The 2,3-difluorophenyl can be used as an intermediate in the preparation of liquid crystal compounds as described in WO 89/08637.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the reaction of a fluorinated or chlorinated aromatic compound with an electrophile after deprotonation of the ortho position relative to the fluorine or chlorine atom with a strong base to prepare a fluorinated or chlorinated aromatic compound substituted in the ortho position relative to the fluorine or chlorine atom, the improvement wherein the fluorinated or chlorinated aromatic compound and at least 10% of the electrophile are initially introduced together in an inert solvent and the strong base is subsequently added at a reaction temperature of −40° C. to +100° C. such that a fluorinated or chlorinated aromatic anion formed as an intermediate by deprotonation is trapped in situ by the electrophile to produce the fluorinated or chlorinated aromatic compound substituted in the ortho position relative to the fluorine or chlorine atom.

2. The process of claim 1 wherein the strong base used is an alkali metal amide.

3. The process of claim 1 wherein the fluorinated or chlorinated aromatic compound substituted in the ortho position relative to the fluorine or chlorine atom prepared by the process is of one of the formulae Ia, Ib or Id:

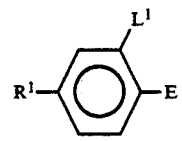  Ia

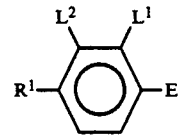  Ib

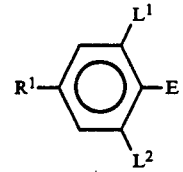  Id wherein E is hydrogen, L$^1$ and L$^2$ are each, independently of one another, F or Cl and R$^1$ is hydrogen, C$_1$–C$_{12}$-alkyl or -alkoxy or a mesogenic radical.

4. A process according to claim 1, wherein the electrophile used is an alkylating or hydoxyalkylating agent.

5. A process according to claim 1, wherein the electrophile used is a silylating agent.

6. A process according to claim 1, wherein the electrophile used is a trialkyl borate.

7. A process according to claim 1, wherein the reaction temperature is between −40°C. and +40° C.

8. A process according to claim 1, wherein the strong base used is an organometallic compound of an alkali metal.

9. A process according to claim 2, wherein the strong base is lithium diisopropylamide.

10. A process according to claim 1, wherein the inert solvent is tetrahydrofuran.

11. A process according to claim 1, wherein 1.2 to 1.8 mol of the base is reacted with 1.0 to 1.3 mol electrophile and 1 mol of the fluorinated and chlorinated aromatic.

* * * * *